United States Patent
Bajus et al.

(10) Patent No.: US 10,093,605 B2
(45) Date of Patent: Oct. 9, 2018

(54) CATALYTIC OXIDATION OF 3,5,5-TRIMETHYLCYCLOHEXA-3-ENE-1-ONE (β-ISOPHORONE) WITH HYDROGEN PEROXIDE TO AFFORD 2,6,6-TRIMETHYL-2-CYCLOHEXENE-1,4-DIONE (KETO-ISOPHORONE)

(71) Applicant: Evonik Degussa GmbH, Essen (DE)

(72) Inventors: Stephanie Bajus, Hanau (DE); Jan Caßens, Recklinghausen (DE); Jens Döring, Dortmund (DE); Jörg-Joachim Nitz, Essen (DE); Stephan Kohlstruk, Gladbeck (DE); Robert Jansen, Bottrop (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 15/822,607

(22) Filed: Nov. 27, 2017

(65) Prior Publication Data
US 2018/0155264 A1 Jun. 7, 2018

(30) Foreign Application Priority Data
Dec. 2, 2016 (EP) .................................... 16201929

(51) Int. Cl.
*C07C 45/28* (2006.01)
(52) U.S. Cl.
CPC .......... *C07C 45/28* (2013.01); *C07C 2601/16* (2017.05)
(58) Field of Classification Search
CPC ............................ C07C 45/28; C07C 2601/16
See application file for complete search history.

(56) References Cited

U.S. PATENT DOCUMENTS

| | | |
|---|---|---|
| 5,874,632 A | 2/1999 | Hahn et al. |
| 6,469,215 B1 | 10/2002 | Krill et al. |
| 8,884,066 B2 | 11/2014 | Orschel et al. |
| 8,889,914 B2 | 11/2014 | Orschel et al. |
| 2002/0025906 A1 | 2/2002 | Hagiya et al. |
| 2016/0152496 A1 | 6/2016 | Kreczinski et al. |
| 2017/0298003 A1 | 10/2017 | Rittsteiger et al. |

FOREIGN PATENT DOCUMENTS

| | | |
|---|---|---|
| DE | 19619570 A1 | 11/1997 |
| DE | 10024264 A1 | 11/2001 |
| WO | 2015177011 A1 | 11/2015 |

OTHER PUBLICATIONS

Kohlstruk et al., U.S. Appl. No. 15/541,733, filed Jul. 6, 2017.
Langkabel et al., U.S. Appl. No. 15/602,723, filed May 23, 2017.
Langkabel et al., U.S. Appl. No. 15/603,966, filed May 24, 2017.
Langkabel et al., U.S. Appl. No. 15/604,118, filed May 24, 2017.
Rittsteiger et al., U.S. Appl. No. 15/642,382, filed Jul. 6, 2017.
Rüfer et al., U.S. Appl. No. 15/604,873, filed May 25, 2017.
Rüfer et al., U.S. Appl. No. 15/604,988, filed May 25, 2017.
Rüfer et al., U.S. Appl. No. 15/605,268, filed May 25, 2017.
European Search Report completed on May 15, 2017 in EP 16 20 1929 (4 pages).

*Primary Examiner* — Sikarl A Witherspoon
(74) *Attorney, Agent, or Firm* — Nexsen Pruet, PLLC; Philip P. McCann

(57) ABSTRACT

The present invention provides a novel process for producing 2,6,6-trimethyl-2-cyclohexene-1,4-dione (keto-isophorone) by catalytic oxidation of 3,5,5-trimethylcyclohexa-3-ene-1-one (β-isophorone) with hydrogen peroxide as the oxidant. In particular, the novel process includes phase transfer reagent in a biphasic system including an organic phase and an aqueous phase wherein the biphasic system includes 1) a tungsten polyoxyometallate as catalyst and hydrogen peroxide, and/or 2) a mixture of a) a mineral acid, b) hydrogen peroxide, and c) a metal tungstate.

20 Claims, No Drawings

CATALYTIC OXIDATION OF 3,5,5-TRIMETHYLCYCLOHEXA-3-ENE-1-ONE (β-ISOPHORONE) WITH HYDROGEN PEROXIDE TO AFFORD 2,6,6-TRIMETHYL-2-CYCLOHEXENE-1,4-DIONE (KETO-ISOPHORONE)

This application claims the benefit of European Application No. 16201929.3 filed on Dec. 2, 2016 the disclosure of which is expressly incorporated herein by reference.

BACKGROUND

The present invention provides a novel process for producing 2,6,6-trimethyl-2-cyclohexene-1,4-dione (keto-isophorone) by catalytic oxidation of 3,5,5-trimethylcyclohexa-3-ene-1-one (β-isophorone) with hydrogen peroxide as the oxidant.

The present invention relates to the epoxidation of 3,5,5-trimethylcyclohexa-3-ene-1-one (β-isophorone, β-IP) and the direct further reaction of this compound to afford 2,6,6-trimethyl-2-cyclohexene-1,4-dione (keto-isophorone) using a catalyst system consisting of a tungsten salt (sodium tungstate), phosphoric acid and a phase transfer reagent in a one-pot synthesis.

Isophorone (IP) is obtained by condensation of acetone—it is the trimeric condensation product. After the reaction a mixture of the isomers 3,5,5-trimethylcyclohexa-2-ene-1-one (α-isophorone) and 3,5,5-trimethylcyclohexa-3-ene-1-one (β-isophorone) (U.S. Pat. No. 8,889,914 B2) is present.

Isomerization of 3,5,5-trimethylcyclohexa-2-ene-1-one (α-isophorone) in the liquid phase in the presence of a homogeneous or heterogeneous catalyst (DE 19639569 A1) makes it possible to produce 3,5,5-trimethylcyclohexa-3-ene-1-one (β-isophorone) in very good yields.

Trimethylhydroquinone diacetate (TMHQ-DA), which may be used as a precursor for the production of vitamin E, may be produced starting from β-IP. Thus, IP provides a route to vitamin E and can in this regard be viewed as an alternative to trimethylphenol which is likewise a precursor of vitamin E.

One important and, for existing processes, economy-determining step for the production of vitamin E starting from isophorone (IP) is the conversion into the intermediate keto-isophorone.

The oxidation of β-isophorone using peroxycarboxylic acids to afford epoxy-isophorone is known from the literature (DE 110024265/U.S. Pat. No. 6,469,215). The examples describe not only the oxidation of β-isophorone but also the production of perpropionic acid from propionic acid and hydrogen peroxide and the conversion of epoxy-isophorone into dihydroketo-isophorone.

However, the large number of reaction steps and process steps to arrive at keto-isophorone and the use of safety-critical peroxycarboxylic acids and costly catalyst systems is a great disadvantage of this method on both economic and safety grounds.

The direct oxidation of β-Isophorone to afford keto-isophorone is also known (DE 19619570). Here, the β-isophorone is oxidized with oxygen using a costly manganese-salen catalyst at elevated pressure (up to 10 bar). The elevated pressure and the requirement for using pure oxygen present a safety engineering challenge for the construction of production plants.

The direct oxidation of α-isophorone to afford ketoisophorone directly is also described in scientific publications (1.) *Catalysis Commun* 11_2010_758-762/2.) *Applied Catalysis A General* 345_2008_104-111. However, the keto-isophorone conversions and selectivities are too low, and the catalysts and/or oxidants used (for example organic peroxo compounds or N-hydroxyphthalimides (NHPI)) too costly, to produce keto-isophorone on a large industrial scale.

SUMMARY

The problem addressed was that of finding a process which does not exhibit the disadvantages as described above and thus finding a simpler method for the production of keto-isophorone.

It has now been found that, surprisingly, the direct conversion of β-isophorone to keto-isophorone in high conversions and yields can be achieved with the aid of tungsten polyoxometallate, so-called POM, catalysts as the active catalyst using hydrogen peroxide as a cost-effective oxidant.

It was found that the keto-isophorone may be formed from β-isophorone directly in a tungsten POM catalysed one-pot oxidation reaction.

DETAILED DESCRIPTION

The present invention provides a process for producing keto-isophorone by catalytic oxidation of β-isophorone in the presence of at least one catalyst and hydrogen peroxide in a one-pot synthesis, wherein the oxidation is effected in the presence of at least one phase transfer reagent in a biphasic system consisting of
A) at least one organic phase
and
B) at least one aqueous phase
wherein the biphasic system comprises:
1) at least one tungsten polyoxyometallate as catalyst and hydrogen peroxide,
and/or
2) a mixture of
a) at least one mineral acid,
b) hydrogen peroxide,
c) at least one metal tungstate.

The aqueous phase contains hydrogen peroxide as the oxidant. The tungsten POM catalyst system may be generated in situ during the reaction (as per 2) or in advance (as per 1). The metal tungstate reacts with the mineral acid, preferably phosphoric acid, and hydrogen peroxide in the aqueous phase to form the tungsten polyoxometallate (POM).

The catalyst tungsten POM is produced from at least one mineral acid, preferably from phosphoric acid, at least one metal tungstate, preferably from the metal sodium, the formation of tungsten polyoxometallate (tungsten POM) then taking place in the presence of hydrogen peroxide.

Tungsten polyoxometallate (tungsten POM) catalysts may be produced in the manner also described in WO2015177011 A1:

Particularly suitable starting materials for the formation of the catalytically active transition metal compound are derivatives of tungsten. Contemplated derivatives include especially an oxide, a mixed oxide, an oxoacid, a salt of an oxoacid, a carbonyl derivative, a sulphide, a chloride, an oxychloride or a stearate of the element tungsten.

Suitable derivatives are for example the metal carbonyls $W(CO)_6$, the oxides $WO_2$, $W_2O_5$, $WO_3$, the sulphides $WS_2$ or $WS_3$. Further examples include the oxo acids $H_2WO_4$ and $H_2MoO_4$ or the alkali metal and alkaline earth metal salts thereof. Particularly suitable are, in particular, salts of tungstic acid, particularly sodium, potassium and ammonium tungstate. The compound particularly suitable for the formation of the catalytically active transition metal compound in situ has proven to be sodium tungstate, $Na_2WO_4$.

The formation of the catalytically active transition metal compound in situ is preferably effected by reaction with a mineral acid of phosphorus. However, the formation of the catalytically active transition metal compound may also be accomplished in a separate reaction wherein initially a transition metal compound described above is reacted with a mineral acid of phosphorus and/or arsenic and also hydrogen peroxide and the thus obtained catalytically active transition metal compound is added to the biphasic system of the epoxidation reaction.

The mineral acid of phosphorus is added to the biphasic system. This forms a catalytically active transition metal compound which comprises both the transition metal and phosphorus.

Particularly effective mineral acids of phosphorus are phosphoric acid, phosphorous acid, polyphosphoric acid, pyrophosphoric acid.

In a particularly preferred embodiment the catalytically active transition metal compound, the catalyst, is formed in situ by reaction of a tungstic acid salt, in particular sodium, potassium or ammonium tungstate, with phosphoric acid and with hydrogen peroxide.

The amount-of-substance ratio of the phosphoric acid to the transition metal is preferably in the range from 0.1 to 10.0, particularly preferably from 0.25 to 5.0 and most preferably from 1 to 2.

The produced catalyst system may be employed in a broad temperature range of 1° C.-200° C.

Due to the poor solubility of β-isophorone in water a phase transfer reagent is required. The phase transfer reagent allows the oxidation-active catalyst species tungsten POM formed by oxidation with hydrogen peroxide to be transferred into the organic phase. The oxidation of the β-IP to afford the keto-isophorone takes place there. The reduced catalyst is subsequently reoxidized by the hydrogen peroxide to afford the tungsten POM in the aqueous phase.

The phase transfer reagent comprises a cation or a compound which forms a cation in the aqueous phase and the cation can form a salt soluble in the organic phase with a peroxotungstate or heteropolyperoxotungstate. The phase transfer reagent preferably comprises a singly charged cation or a compound which forms a singly charged cation in the aqueous phase.

Suitable phase transfer catalysts are quaternary ammonium salts, tertiary amines or quaternary phosphonium salts.

Suitable quaternary ammonium salts are tetraalkylammonium salts having a total of at least 12 carbon atoms in the alkyl groups, for example, dodecyltrimethylammonium salts, hexadecyltrimethylammonium salts, octadecyltrimethylammonium salts, methyltributylammonium salts and methyltrioctylammonium salts. Also suitable are quaternary ammonium salts comprising mono- or divalent anions, for example chloride, bromide, nitrate, sulphate, hydrogenphosphate, dihydrogenphosphate, methylsulphonate, methylsulphate and ethyl sulphate.

Suitable tertiary amines are dodecyldimethylamine, hexadecyldimethylamine, octadecyldimethylamine, tributylamine and trioctylamine.

Suitable quaternary phosphonium salts are alkyl-, benzyl- and phenylphosphonium salts, these include for example di-tert-butylmethylphosphonium tetrafluoroborate, benzyltriphenylphosphonium chloride and triphenylbutylphosphonium chloride.

The preferably employed catalyst system consists of sodium tungstate, phosphoric acid and a phase transfer reagent, preferably trioctylamine, which under the reaction conditions is protonated to form the corresponding ammonium salt.

The oxidation of the β-isophorone to afford the keto-isophorone proceeds in a plurality of steps:
1. Epoxidation of the β-isophorone (A) to afford the epoxide (B),
2. Rearrangement of the epoxide (B) to afford the hydroxy-isophorone. (HIP), (C),
3. Oxidation of the HIP to afford the keto-isophorone. (KIP), (D).

Formula 1:

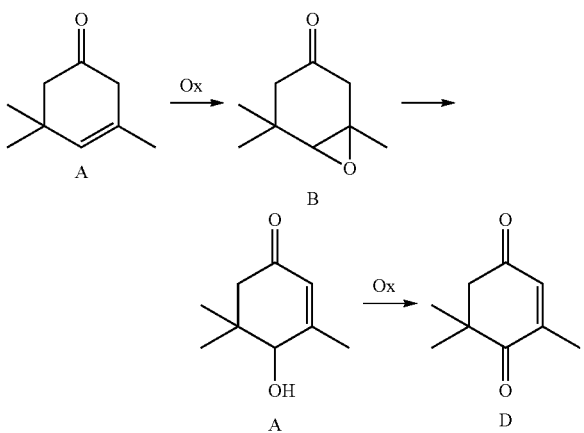

Reaction mechanism of the tungsten POM catalysed oxidation of β-isophorone (A) with hydrogen peroxide as the oxidant (OX)

The oxidation of the β-isophorone to afford the keto-isophorone may be effected under the following conditions:

The temperature varies from 30-120° C., preferably in the range between 50-80° C.

The ratio of β-isophorone to $H_2O_2$ is 1:0.7-1:3 wt %, preferably 1:1-1:2.2 wt %.

The ratio of organic phase (in particular β-isophorone. HIP, KIP) to aqueous phase (in particular water & $H_2O_2$) varies from 1:10 to 5:1 wt %, preferably 1:4-2:1 wt %.

The $H_2O_2$ concentration in the aqueous phase is 1-50 wt %, preferably 2-30 wt %.

The molar ratio of catalyst (tungsten POM) to $H_2O_2$ is 1:10-1:400, preferably 1:50-1:200.

EXAMPLES

General Procedure for Examples (Inventive)

A 50 ml three-necked round bottom flask fitted with a reflux cooler and stirrer is initially charged with a mixture of $Na_2WO_4 \times 2\ H_2O$, $H_3PO_4$, phase transfer reagent (PTC), β-isophorone and water and the mixture is heated to reaction temperature (T). After achieving the reaction temperature the required amount of the 30% hydrogen peroxide is metered into the flask over 5 minutes using a syringe. The reaction mixture is then stirred for the remaining reaction time. At the end of the run the mixture is cooled with continuous stirring and homogenized with dioxane. The mixture is then analyzed by gas chromatography, NMR (determination of organic compounds) and cerimetry ($H_2O_2$ analysis).

The aim here was to achieve the highest possible conversion (C) of β-isophorone and, simultaneously, a high yield (A) of oxidation products (HIP+KIP). The degree of $H_2O_2$ utilization (quotient of the sum of amount-of-substance quantities of KIP+HIP and employed amount-of-substance quantity of $H_2O_2$) also plays an important role for an efficient process. Factors of influence varied were:

phase transfer reagent (examples 1-4)
temperature (examples 4-6)
$H_2O_2$ amount (examples 4 & 7)

Reaction Conditions:

50 ml round bottom flask, 2.5 g β-isophorone (18 mmol), 2.25-4.5 g 30% $H_2O_2$ solution (aqueous, 40 mmol), tungsten POM catalyst (100 mg $Na_2WO_4$×2 $H_2O$ (0.3 mmol), 200 mg $H_3PO_4$ (85%, 1.7 mmol), 0.23 mmol), phase transfer reagent (1. none/2. Rewoquat CR 3099/3. trioctylmethylammonium methylsulphate (TMAMS), 4. trioctylamine), 5 g water, pH=2, duration=2 h, temperature 70-90° C. The respective reaction conditions for examples 1-9 of the tungsten polyoxometallate catalysed oxidation of β-isophorone with hydrogen peroxide are summarized in table 1.

Examples 1-4 (Variation of Phase Transfer Reagent)

The results with different phase transfer reagents are reported in table 1 (entries 1 to 4). The conversion of the isophorone into keto-isophorone is a two-stage oxidation as a result of which a 2.2-fold excess of $H_2O_2$ based on β-isophorone was employed, the reaction temperature (T) was 80° C.

Without a phase transfer reagent the target reaction proceeds only very slowly. The β-isophorone is predominantly isomerized into α-isophorone and converted into undesired byproducts (table 1 entry 1).

The use of trioctylamine as the PTC, which under the reaction conditions is protonated to afford the corresponding ammonium salt, achieved the highest yield of keto-isophorone (table 1 entry 4). The conversion of β-isophorone was virtually complete (C=99%) and the yield (Y) of keto-IP was 42%. However, α-isophorone (yield: 10%) and in particular hydroxyl-isophorone (yield 35%) also represent a product of value since in a continuous production process these may be separated from the remaining reaction mixture and recycled back into the production process. α-isophorone may be isomerized into β-isophorone again and HIP may be returned to the reaction directly to be further oxidized to afford keto-IP. Thus, the yield for the sum of the oxidized molecules (HIP and KIP) is then 77% The yield for products of value (α-isophorone, HIP and KIP) is even 87%.

Examples 4-6 (Variation of Temperature)

The results at different temperatures (70-90° C.) are reported in table 1 (entry 4 to 6). The conversion of the isophorone into keto-isophorone was in turn performed with a 2.2-fold excess of $H_2O_2$ based on β-isophorone and trioctylamine was employed at the phase transfer reagent.

A reaction temperature of 70° C. resulted in a lower KIP yield (24%) but in an increased HIP yield (67%). The yield for the sum of the oxidized molecules (HIP and KIP) is then 91% and is 14% higher than at a reaction temperature of 80° C.; the degree of $H_2O_2$ utilization also increases slightly to 53%.

By contrast, at a reaction temperature of 90° C. undesired byproducts/descendant products are formed to a greater extent, the sum of KIP- and HIP-yield falls to 72% and the degree of $H_2O_2$ utilization also falls slightly to 48%.

Examples 4 & 7 (Variation of $H_2O_2$ Amount)

The degree of $H_2O_2$ utilization can be increased markedly by reducing the employed $H_2O_2$ amount. The difference between $H_2O_2$ conversion and $H_2O_2$ utilization can be explained by decomposition and the formation of byproducts/descendant products; this applies to all examples (Examples 1-7).

Reducing the employed $H_2O_2$ amount by 50% to 1.1 times the isophorone amount-of-substance quantity increases the degree of $H_2O_2$ utilization to up to 85%! Yet, the sum of the oxidized molecules (HIP and KIP) remains at a very good 76%.

CONCLUSION 2,6,6-trimethyl-2-cyclohexene-1,4-dione (keto-isophorone) can be produced efficiently in a one-pot synthesis by catalytic oxidation of 3,5,5-trimethylcyclohexa-3-ene-1-one (beta-isophorone) with hydrogen peroxide as the oxidant. Not only keto-isophorone (KIP) but also hydroxy-isophorone (HIP), which may be separated from the remaining reaction mixture and further oxidized to afford keto-isophorone in a continuous process, are formed.

A yield of oxidized molecules (HIP and KIP) of up to 91% was achieved with the employed catalyst system consisting of sodium tungstate, phosphoric acid and trioctylamine as the phase transfer reagent. In addition to the very good yields for products of value (HIP+KIP) the degree of $H_2O_2$ utilization of up to 85% is also excellent.

TABLE 1

| Entry | PTC | m β-IP [g] | m $H_2O_2$ (30%) [g] | T [° C.] | C (β-IP) [%] | Y (α-IP) [%] | Y (KIP) [%] | Y (HIP) [%] | C ($H_2O_2$) [%] | $H_2O_2$ Utilization [%] |
|---|---|---|---|---|---|---|---|---|---|---|
| 1 | — | 2.5 | 4.5 | 80 | 65 | 22 | 5 | 13 | 31 | 10 |
| 2 | Rewoquat | 2.5 | 4.5 | 80 | 98 | 8 | 24 | 52 | 90 | 46 |
| 3 | TMAMS | 2.5 | 4.5 | 80 | 97 | 8 | 29 | 24 | 72 | 38 |
| 4 | Trioctylamine | 2.5 | 4.5 | 80 | 98 | 10 | 42 | 35 | 80 | 51 |
| 5 | Trioctylamine | 2.5 | 4.5 | 70 | 99 | 8 | 24 | 67 | 86 | 53 |
| 6 | Trioctylamine | 2.5 | 4.5 | 90 | 99 | 15 | 46 | 16 | 90 | 48 |
| 7 | Trioctylamine | 2.5 | 2.25 | 80 | 95 | 13 | 15 | 61 | 98 | 85 |

50 ml round bottom flask, 2.5 g beta-isophorone (18 mmol), 2.25-4.5 g 30% $H_2O_2$ solution (aqueous, 20-40 mmol), (100 mg $Na_2WO_4$ × 2 $H_2O$ (0.3 mmol), 200 mg $H_3PO_4$ (85%, 1.7 mmol), 0.23 mmol phase transfer reagent (PTC), 5 g water, pH range = 1.5-2, 2 h.

The invention claimed is:

1. A process for producing keto-isophorone, the process comprising the step of oxidizing β-isophorone in the presence of a catalyst and hydrogen peroxide in a one-pot synthesis, in the presence of a phase transfer reagent in a biphasic system comprising
A) an organic phase
and
B) an aqueous phase
wherein the biphasic system comprises:
 1) a tungsten polyoxyometallate as catalyst and hydrogen peroxide,
 and/or
 2) a mixture of
  a) a mineral acid,
  b) hydrogen peroxide, and
  c) a metal tungstate.

2. The process according to claim 1, wherein the oxidizing is performed at a temperature of from 30 to 120° C.

3. The process according to claim 1, wherein the ratio of β-isophorone to $H_2O_2$ is from 1:0.7 to 1:3 wt %.

4. The process according to claim 1, wherein the ratio of organic phase to aqueous phase varies from 1:10 to 5:1 wt %.

5. The process according to claim 1, wherein the hydrogen peroxide concentration in the aqueous phase is from 1 to 50 wt %.

6. The process according to claim 1, wherein the molar ratio of catalyst to hydrogen peroxide is from 1:10 to 1:400 wt %.

7. The process according to claim 1, wherein the phase transfer agent is selected from the group consisting of quaternary ammonium salts, tertiary amines or quaternary phosphonium salts, alone or in mixtures.

8. The process according to claim 7, wherein the phase transfer agent is selected from the group consisting of dodecyltrimethylammonium salts, hexadecyltrimethylammonium salts, octadecyltrimethylammonium salts, methyltributylammonium salts, methyltrioctylammonium salts, dodecyldimethylamine, hexadecyldimethylamine, octadecyldimethylamine, tributylamine, trioctylamine, alkyl-, benzyl- and phenylphosphonium salts, alone or in mixtures.

9. The process according to claim 1, wherein the mineral acid is selected from the group consisting of phosphoric acid, phosphorous acid, polyphosphoric acid, pyrophosphoric acid, alone or in mixtures.

10. The process according to claim 1, further wherein the metal tungstate is selected from the group consisting of sodium tungstate, potassium tungstate, and ammonium tungstate.

11. The process according to claim 1, wherein the biphasic system consists of sodium tungstate, phosphoric acid and a phase transfer reagent.

12. The process according to claim 1, wherein the phase transfer agent is trioctylamine.

13. The process according to claim 1, wherein the oxidizing is performed at temperatures of from 50 to 80° C.

14. The process according to claim 1, wherein the ratio of β-isophorone to $H_2O_2$ is from 1:1 to 1:2.2 wt %.

15. The process according to claim 1, wherein the ratio of organic phase to aqueous phase varies from 1:4 to 2:1 wt %.

16. The process according to claim 1, wherein the $H_2O_2$ concentration in the aqueous phase is from 2 to 30 wt %.

17. The process according to claim 1, wherein the molar ratio of catalyst to $H_2O_2$ is from 1:50 to 1:200 wt %.

18. The process according to claim 2, wherein the mineral acid is selected from the group consisting of phosphoric acid, phosphorous acid, polyphosphoric acid, pyrophosphoric acid, alone or in mixtures, are employed as the mineral acids.

19. The process according to claim 2, wherein sodium, potassium and/or ammonium tungstate.

20. The process according to claim 7, wherein the phase transfer agent is selected from the group consisting of di-tert-butylmethylphosphonium tetrafluoroborate, benzyltriphenylphosphonium chloride and triphenylbutylphosphonium chloride, alone or in mixtures.

* * * * *